United States Patent [19]

Buzza et al.

[11] 4,170,523
[45] Oct. 9, 1979

[54] METHOD FOR CHECKING ISOLATION BETWEEN TITRATION AND ELECTROCHEMICAL MEASURING SYSTEMS OF A CHEMICAL ANALYZER

[75] Inventors: Edmund E. Buzza, Fullerton; John E. Lillig, Diamond Bar, both of Calif.

[73] Assignee: Beckman Instruments, Inc., Fullerton, Calif.

[21] Appl. No.: 902,126

[22] Filed: May 2, 1978

Related U.S. Application Data

[63] Continuation of Ser. No. 738,791, Nov. 4, 1976, abandoned.

[51] Int. Cl.$^2$ .................... G01N 27/44; G01N 27/46; G01R 31/00
[52] U.S. Cl. ............................ 204/1 T; 204/195 R; 204/195 P; 204/195 T; 324/51
[58] Field of Search ............ 324/51; 204/1 T, 195 R, 204/195 P, 195 T; 23/230 R, 253 R

[56] References Cited

U.S. PATENT DOCUMENTS

| 3,661,748 | 5/1972 | Blackmer | 204/1 T X |
| 3,718,568 | 2/1973 | Neuwelt | 204/195 P |
| 3,719,576 | 3/1973 | Macur | 204/195 P |
| 4,003,705 | 1/1977 | Buzza et al. | 23/230 R |

Primary Examiner—G. L. Kaplan
Attorney, Agent, or Firm—Robert J. Steinmeyer; Robert R. Meads; John R. Shewmaker

[57] ABSTRACT

A method of checking the electrical isolation provided by a gas permeable membrane for a carbon dioxide sensor in an analyzer for simultaneously measuring the carbon dioxide and chloride content of a blood sample as it reacts with a reagent in a sample cell. The method involves actuating the carbon dioxide sensor during its normal "off-time" and measuring any signal generated thereby while a coulometric generator in the analyzer is initially activated to titrate to a repeatable initial value any chloride present in the reagent alone. Any signal generated by the sensor above a predetermined value is indicative of a defective membrane and may be utilized to inhibit further operation of the analyzer.

4 Claims, 2 Drawing Figures

METHOD FOR CHECKING ISOLATION BETWEEN TITRATION AND ELECTROCHEMICAL MEASURING SYSTEMS OF A CHEMICAL ANALYZER

This is a continuation of application Ser. No. 738,791, filed Nov. 4, 1976, now abandoned.

BACKGROUND OF THE INVENTION

1. Field of the Invention

The present invention relates generally to the detection of defects in selectively permeable barriers through which electrochemical sensors communicate with a sample material to be analyzed and, more particularly, to a method for checking the integrity of such a barrier associated with a sensor incorporated in an electrochemical titrator.

2. Description of the Prior Art

Copending U.S. Pat. application Ser. No. 586,435 (now U.S. Pat. No. 4,003,705), by Buzza et al., and assigned to the assignee of the present invention, describes an electrochemical analysis apparatus for measuring both chloride and carbon dioxide in blood. The blood sample is reacted with an acid reagent in a sample chamber to release carbon dioxide which diffuses through a gas permeable membrane to a carbon dioxide sensor. The sensor includes an alkaline reagent which undergoes a change in pH upon reaction with the carbon dioxide and a pH measuring electrode arrangement for measuring the resulting pH change to provide a measure of the carbon dioxide concentration. Specifically, the pH signal is differentiated to provide an instantaneous time rate of change of pH signal which is measured to determine the carbon dioxide value.

For chloride detection, the aforementioned apparatus includes titration apparatus comprising coulometric generator electrodes and amperometric detector electrodes communicating with the sample chamber for titrating the sample chloride. To this end the coulometric generator electrodes are energized to generate silver ions which combine with the sample chloride to precipitate silver chloride. The completion of the silver chloride precipitation is detected by the amperometric detector electrodes and the total coulometric current flow required to precipitate the silver chloride provides a measure of the chloride originally in the sample. To ensure that the measured coulometric current represents titration of the sample chloride only, the coulometric generator is energized prior to sample introduction to precipitate out chloride which may be present in the acid reagent to establish an initial or base line chloride level in the sample chamber prior to the introduction of each sample.

It is critically important that the selectively permeable membrane permit the passage of carbon dioxide to the carbon dioxide sensor but reject all other substances which could adversely affect operation of the carbon dioxide sensor. Moreover, the membrane must provide electrical isolation between the carbon dioxide sensor and the titration circuitry. If the membrane includes pin holes or other defects which permit reagent leakage through or around the membrane to the carbon dioxide sensor or which permit electrical cross-talk between the carbon dioxide measuring and chloride measuring systems, then erroneous sample measurements will result. Typically, for adequate isolation a membrane should exhibit an impedance of about $10^9$ ohms or more.

Several proposals have been advanced in the past for monitoring the isolation integrity (i.e. impedance) of selectively permeable membranes in electrochemical sensor arrangements. In one approach an a.c. signal is superimposed across the membrane and a.c. detector and demodulation circuitry is provided to monitor the a.c. signal transmitted by the membrane. In another approach a separate monitoring electrochemical half cell and associated monitoring circuitry is provided for developing a signal across the membrane indicative of a fault in the membrane. While each of these approaches is generally satisfactory for the purpose intended, each requires the addition of independent and complex electrical monitoring circuitry and components which reduces the overall attractiveness of each for commercial implementation particularly for combined electrochemical sensing and titration apparatus as described above. As a result, a need exists for a simple and inexpensive technique for checking the integrity of a selectively permeable barrier in such apparatus.

SUMMARY OF THE INVENTION

The present invention resides in a new and improved method for checking the impedance of a selectively permeable barrier associated with an electrochemical sensor in combined sensing and titration apparatus. The method overcomes the disadvantages of the prior approaches and does so in a manner which is simple and straightforward in operation and readily adapted for commercial implementation.

In accordance with a primary aspect of the present invention, applicants have discovered that in combined titration and electrochemical sensing apparatus, if the electrochemical sensor and the coulometric generator of the titrator are both enabled during a period prior to introduction of sample into the sample chamber, the signal then derived from the electrochemcial sensor indicates the degree of isolation provided by the barrier means separating the electrochemical sensor from the sample chamber. In apparatus where the sample is reacted with a reagent previously introduced into the sample chamber, the coulometric generator means may be enabled to titrate a constituent of the reagent to an initial or base line value before the sample is introduced, and the electrochemical sensor is preferably enabled at this time to check the barrier means.

Measuring circuitry coupled to the electrochemical sensor includes means for differentiating the output signal from the sensor and threshold detection means for measuring a predetermined threshold value of the differentiated signal. The measuring circuitry generates a control signal in response to a differentiated output signal above the predetermined threshold value and the control signal is employed to inhibit further operation of the analyzer.

BRIEF DESCRIPTION OF THE DRAWINGS

FIG. 2 is a combined diagrammatic and electrical schematic diagram of the apparatus for checking the

DESCRIPTION OF THE PREFERRED EMBODIMENT

Figure 1:
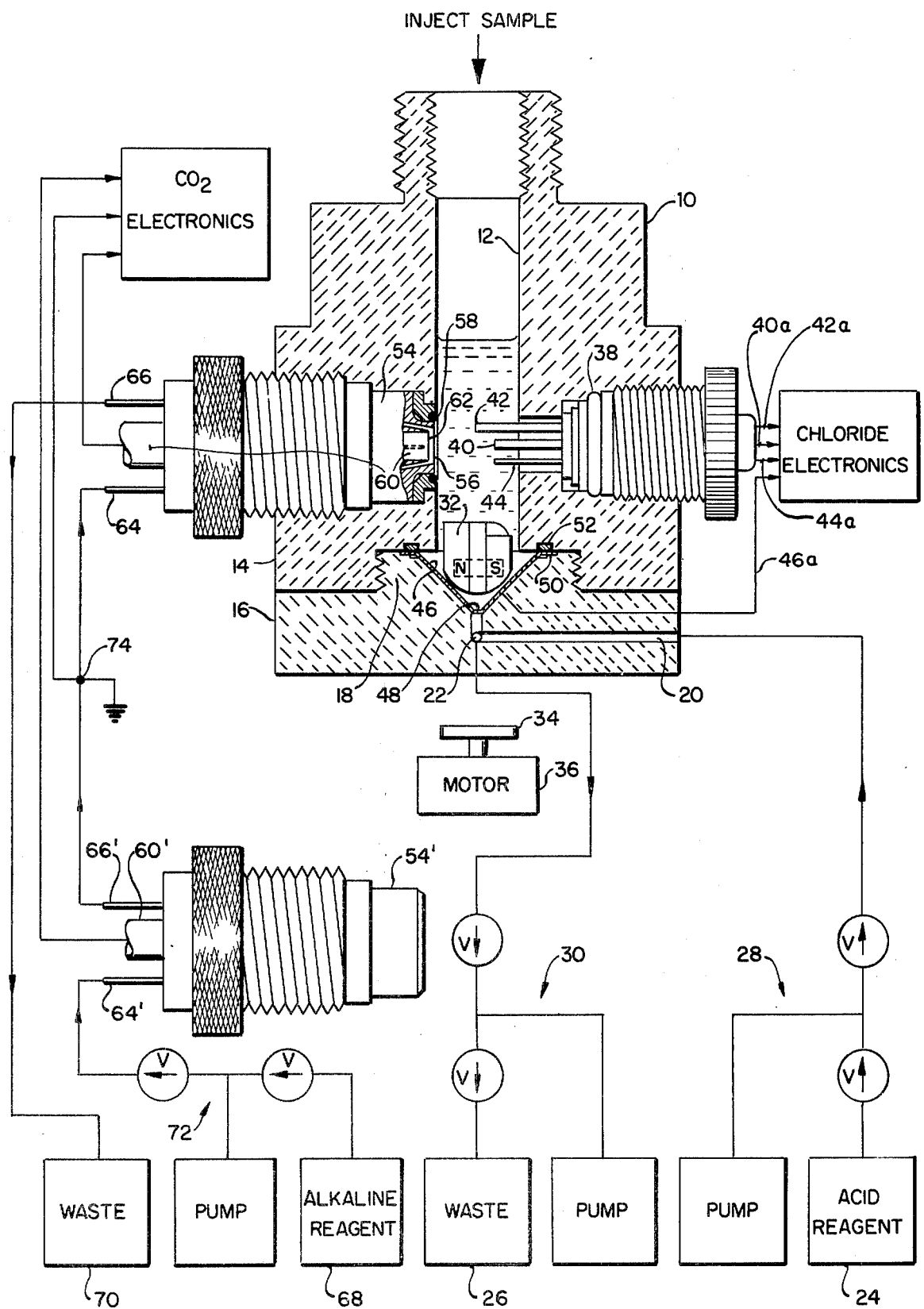
FIG. 1 is a longitudinal sectional view, taken in a generally vertical plane, through a sample cup employed in the electrochemical analysis apparatus employed with the present invention and illustrates the mounting of chloride determining electrodes and a carbon dioxide measuring sensor, the sensor being partially cut-away, together with associated reagent pumping systems.

FIG. 1 of the drawings illustrates an electrochemical analysis apparatus of the type described in aforementioned copending patent application Ser. No. 586,435 which represents one preferred apparatus for practicing the present invention. The prior apparatus will be described to the extent necessary for an understanding of the present invention and reference should be made to the copending application for additional details concerning the apparatus.

The analysis apparatus of FIG. 1 includes an analysis cell 10 formed from a block of insulating material such as polymethylmethacrylate. A cylindrical, vertically extending chamber 12, open at its upper end, is formed in the block. A sample such as blood to be analyzed may be injected into the chamber through the upper end thereof by means of a pipette or burette in a conventional manner. The analysis cell is preferably formed from upper and lower mating sections 14 and 16, respectively. Lower section 16 has an upstanding, threaded, central hub 18 which is threaded into upper section 14 to secure the two sections together. The lower surface of the sample chamber is formed in the shape of an inverted cone in the upper surface of the hub 18. A pair of passages 20 and 22 lie in a generally horizontal plane in the lower section and intersect one another at a right angle at the apex of the conical lower surface of the chamber (passage 20 is disposed perpendicular to the plane of the figure). Both passages communicate with the chamber 12 at the apex of the lower surface. Acid reagent, such as sulfuric acid, from reservoir 24 is supplied to the chamber 12 through passage 20 and the contents of the cell, including reagent, sample and the like, are drained from the cell through passage 18 to a waste receptacle 26. Conventional pumping and valving arrangements 28 and 30 are employed to respectively deliver reagent to the cell and to drain the contents of the cell. A conventional magnetic stirring element 32 positioned in the chamber is adapted to be rotated by a magnet 34 positioned below the cell 10 and rotated by means of a motor 36 to mix the contents of the chamber 12.

Titration apparatus for titrating the chloride in the sample is embodied in an electrode module 38 comprising amperometric anode 40, amperometric cathode 42, and coulometric cathode 44 disposed in a horizontal bore in the wall of the analysis cell 10 with the electrodes extending into the sample chamber 12 through a reduced diameter section of the bore. The structure of the electrode module 38 may take the form disclosed in our copending U.S. Pat. application Ser. No. 595,207 filed July 11, 1975, (now U.S. Pat. No. 4,007,105), by Buzza et al. and reference may be had to this application for further details of the module 38.

The fourth and remaining electrode of the titration apparatus, coulometric anode 46, is disposed at the bottom of the chamber 12 and is conically configured to conform to the bottom chamber surface. In addition anode 46 has an opening 48 at the apex thereof aligned with the flow passage thereat and through which the chamber is filled and drained. The base of the conical anode 46 has a horizontally extending, circumferential lip 50 which abuts an O-ring 52 recessed in upper section 14 of the analysis cell 10 to provide a fluid seal between the two sections of the cell.

Electrical connection is made to the anode 50 through a passage (not shown) in the lower cell section 16 by means of a conductor 46a. Corresponding conductors 40a, 42a and 44a are connected to the remaining electrodes, and the four conductors serve to connect the amperometric pair of electrodes to a conventional amperometric detector (88, FIG. 2) and to connect the pair of coulometric electrodes to a conventional coulometric generator (90, FIG. 2).

The apparatus for detecting the carbon dioxide of the sample is identical to that shown in the aforementioned copending patent application Ser. No. 586,435 and comprises first and second electrochemical sensors 54 and 54'. Sensor 54 is illustrated mounted within a horizontal bore of the analysis cell 10 and in communication with the sample chamber 12 thereof through a selectively permeable barrier which, for the measurement of a gas such as carbon dioxide, is a gas permeable, ion-impermeable membrane 56 which is held in place over the end of the sensor by an annular retaining ring 58. Suitable materials for membrane 56 are silicone rubber, polyethylene, or polytetrafluoroethylene. Sensor 54' is identical in construction to sensor 54; however sensor 54' is not mounted in communication with chamber 12 through its corresponding membrane 56'. Rather, sensor 54' may be mounted in a blind bore in cell 10 as taught in aforementioned application Ser. No. 586,435.

Sensor 54 further comprises a conventional pH sensing electrode 60 spaced slightly (on the order of 0.005 inches) from the membrane 56 to define an electrolyte film space 62 between one end of the pH electrode and the membrane. A pair of stainless steel tubes 64 and 66 extend longitudinally within the sensor 54 and are in fluid communication with opposite sides of the electrolyte film space 62.

A series electrolyte flow path is provided through both measuring sensors 54 and 54' from an alkaline electrolyte reservoir 68, containing potassium bicarbonate for example, to a second waste receptacle 70. A conventional pump and valving arrangement supplies reagent from reservoir 68 to the inlet tube 64' of sensor 56'. The outlet tube 66' of sensor 56', in turn, is connected to the inlet tube 64 of sensor 54. The outlet tube 66 of sensor 54 is then connected to the waste receptacle 70. Electrolyte is pumped from reservoir 68 along the series path through each sensor after each sample measurement. As a result, the electrolyte film space 62 of sensor 54 is purged of old reagent and replaced by new reagent which rapidly equilibrates the pH electrode 60 in preparation for the next sample injection and measurement.

A solution ground terminal 74, such as a piece of stainless steel, is provided in the electrolyte flow path either between sensors 54 and 54' or between snesor 54' and reservoir 68. The ground terminal 74 together with output conductors from pH electrodes 60 and 60' are connected to supply corresponding signals to the carbon dioxide measuring electronics.

Figure 2:
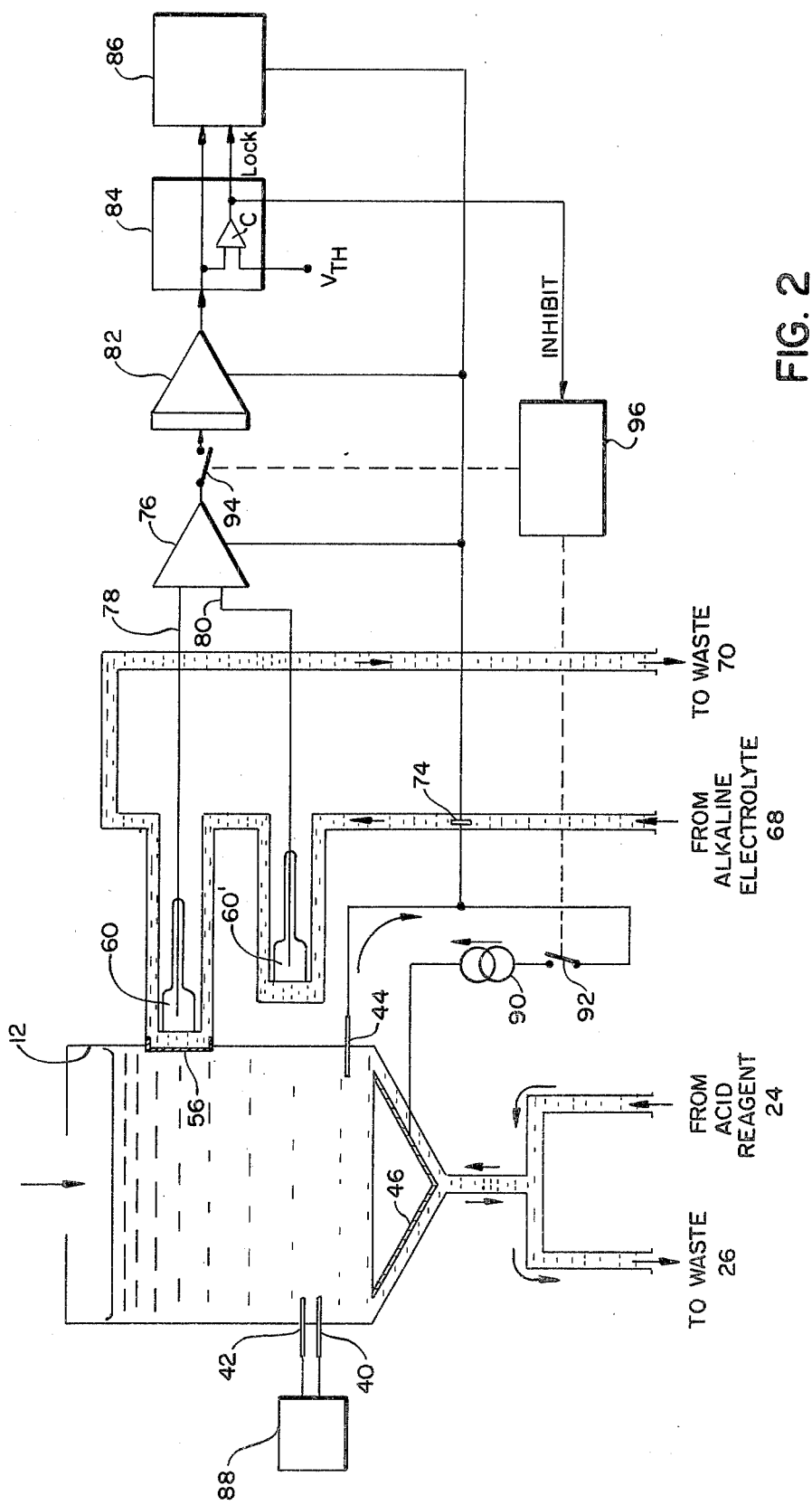

FIG. 2 illustrates the apparatus of FIG. 1 in diagrammatic form and includes, in block diagram form, the circuitry for measuring carbon dioxide and for checking the isolation integrity of the selectively permeable membrane 56 of sensor 54. In FIG. 2 reference numerals corresponding to those in FIG. 1 have been utilized to identify the same features.

The carbon dioxide measuring circuitry is identical to that described in the aforementioned copending patent application 586,435 and comprises a differential amplifier 76 having first and second input terminals 78 and 80 receiving the respective output signals from the pH electrodes 60 and 60'. The output of differential amplifier 76 is connected to differentiator circuit 82 which differentiates the differential pH signal from amplifier 76 to derive a signal at its output proportional to the instantaneous time rate of change of pH. The output of differentiator circuit 82, in turn, is connected to a peak pick and hold amplifier 84 which senses a maximum value of the time rate of change signal and derives an output to a digital display 86. The differentiator and amplifier circuits may take the form illustrated and described in "Glucose Analyzer Service Manual", Beckman Instruction 83544-B), copyright 1970 by Beckman Instruments, Inc.

In FIG. 2 the amperometric detector electrodes 40 and 42 are shown connected to conventional amperometric detector circuitry 88 while coulometric generator electrodes 44 and 46 are shown connected to a conventional coulometric current generating source 90. Current source 90, when activated, serves to liberate silver ions from coulometric anode 46 which combine with the chloride in the cell 12 to precipitate silver chloride in a conventional manner.

In accordance with an important aspect of the present invention, the coulometric current generating means and the electrochemical pH sensors and associated measuring circuitry are activated prior to introduction of a sample into the chamber 12 in order to check the isolation afforded by membrane 56.

Coulometric generator is activated by closing the switch 92 in series with current source 90 while the pH measuring system is activated by closing switch 94 illustrated between amplifier 76 and differentiator 82. Operation of switches 92 and 94 is under the direction of a control 96 which may be manually operated or programmed by well known logic techniques to perform the membrane checking function.

In practice, prior to measuring a sample, the chamber 12 is drained and filled twice with acid reagent from reservoir 24 in order to thoroughly rinse the chamber. Thereafter, the chamber is filled with about one milliliter of acid reagent into which a 10 microliter blood sample will be subsequently injected. Prior to injection of the sample, however, control 96 operates to close switch 92 to enable the coulometric current generator to titrate chloride present in the reagent to a predetermined base line value which is repeatable for each sample to be measured. Typically the coulometric generator is enabled to generate a current pulse for a period of approximately eight seconds to perform this initial titration. Normally, during the titration of the chloride present in the reagent, the pH sensors are inactive. Thus, as far as the carbon dioxide sensing portion of the analyzer is concerned, the reagent chloride titration period has in the past in effect been "off-time". In accordance with the present invention, however, control 96 further operates to close switch 94 and activate the pH measuring sensors 60 and 60' and associated measuring circuitry 78-86 during the period of coulometric current generation prior to sample introduction. If membrane 56 is defective, that is if pin holes or other defects reduce the impedance of the membrane, an apparent $\Delta$ pH signal will be derived across pH electrodes 60 and 60', supplied as an input signal to differential amplifier 76, differentiated by differentiator 82, and supplied to peak pick and hold amplifier 84.

Peak pick and hold amplifier 84 further includes a conventional comparator C for determining when the signal received by amplifier 84 exceeds a predetermined value. The comparator C includes a first input terminal which receives the signal from differentiator 82 and a second terminal supplied with a threshold voltage level $V_{TH}$ establishing the minimum voltage value indicative of a satisfactory membrane 56. When the voltage from differentiator 82 supplied to the first input terminal of comparator exceeds $V_{TH}$, the signal at output terminal of the comparator changes state to supply a control signal indicative of a defective membrane. The control signal is supplied to display 86 to lock the peak output value of the differentiator into the display in a conventional manner thus indicating a defective membrane and the severity of the isolation breakdown. In addition, the control signal is supplied to control 96 which then inhibits further operation of the analyzer by opening switches 92 and 94 to prevent both the chloride and carbon dioxide measuring systems from operating. Thereafter, the defective membrane is replaced.

If membrane 56 if found to be satisfactory, the sample is then injected into the reagent filled chamber 12 by an operator and simultaneous chloride and carbon dioxide measurements are taken for the sample.

Thus it is seen that an apparent $\Delta$ pH response during coulometric titration prior to sample introduction will really be an indication of an isolation breakdown of membrane 56 due to pin holes or other defects in the membrane. Differentiating the apparent $\Delta$ pH signal to obtain the rate of change of pH increases the detection sensitivity of such membrane failure. This is because differentiating the pH signal essentially amplifies the abrupt pH signal change caused by that portion of the coulometric generator signal being transmitted through the membrane. Furthermore, the level of the differentiated signal is independent of the steady pH level which existed between the two pH electrodes prior to the coulometric titration. This allows the establishment of an absolute fault level based on the differentiated signal itself.

While a preferred embodiment of the invention has been illustrated and described, it will be apparent that modifications may be made therein within the scope of the appended claims.

What is claimed is:

1. The method of operating a combined titration and electrochemical sensing apparatus of the type including an analysis cell having a chamber into which a reagent and a sample material to be analyzed are introduced, coulometric generating means for generating ions combinable with a constituent of said sample material to titrate the same, amperometric detector means for detecting the extent of ion combination with said constituent for providing a measurement of said constituent, and electrochemical sensing means communicating with said chamber and the contents thereof through barrier means which is selectively permeable to a substance in the chamber for detecting said substance to provide a measurement thereof, said method comprising prior to introducing said sample material into said chamber the steps of:

introducing said reagent into said chamber;
enabling said coulometric generating means to titrate a constituent of said reagent toward a predetermined value;

enabling said electrochemical sensing means during the period that said coulometric generating means is enabled for detecting transmission of the signal produced by said coulometric generating means across said barrier means to said electrochemical sensing means;

measuring the signal detected by said electrochemical sensing means in response to said coulometric generating means to determine the isolation provided by said barrier means between said chamber and said electrochemical sensing means for deriving an indication of the integrity of said barrier means;

generating a control signal indicative of a fault in said barrier means if the measure of said detected signal exceeds a predetermined value; and if no fault is indicated in said barrier means, subsequently introducing said sample material into said chamber and said reagent therein and enabling said electrochemical sensing means to detect and measure said substance in said chamber.

2. The method of claim 1 including the further step of inhibiting operation of said titration apparatus in response to said control signal.

3. The method of claim 1 wherein said electrochemical sensing means of said titration apparatus includes means for differentiating the signal derived in response to said substance of said sample material and means for measuring a preselected value of said differentiated signal to determine the concentration of said substance, wherein said step of measuring the signal detected by said electrochemical sensing means in response to said coulometric generating means includes the steps of enabling said differentiating means to differentiate the latter signal and generating said control signal indicative of a fault in said barrier means when the latter differentiated signal exceeds said predetermined value.

4. The method of claim 3 wherein said control signal indicative of a fault in said barrier means is generated if a peak value of said latter differentiated signal exceeds said predetermined value.

* * * * *